(12) United States Patent
Nicoletti

(10) Patent No.: US 9,156,598 B2
(45) Date of Patent: Oct. 13, 2015

(54) PACKAGING STRUCTURE FOR CONTAINERS FOR PHARMACEUTICAL USE

(75) Inventor: Fabiano Nicoletti, Mira Venezia (IT)

(73) Assignee: Stevanato Group International A.S., Bratislava (SK)

( * ) Notice: Subject to any disclaimer, the term of this patent is extended or adjusted under 35 U.S.C. 154(b) by 69 days.

(21) Appl. No.: 13/377,412

(22) PCT Filed: Apr. 29, 2011

(86) PCT No.: PCT/EP2011/056861
§ 371 (c)(1),
(2), (4) Date: Dec. 9, 2011

(87) PCT Pub. No.: WO2011/135085
PCT Pub. Date: Nov. 3, 2011

(65) Prior Publication Data
US 2013/0048531 A1  Feb. 28, 2013

(30) Foreign Application Priority Data

Apr. 30, 2010  (IT) .............................. MI2010A0747

(51) Int. Cl.
*B65D 85/00*  (2006.01)
*B65D 77/04*  (2006.01)
*A61M 5/00*  (2006.01)
*B01L 9/06*  (2006.01)
(Continued)

(52) U.S. Cl.
CPC ............. *B65D 77/046* (2013.01); *A61M 5/002* (2013.01); *A61M 5/008* (2013.01); *B01L 9/06* (2013.01); *B65D 77/0446* (2013.01); *B65D 77/20* (2013.01); *B65D 85/42* (2013.01); *B01L 2200/023* (2013.01); *B01L 2300/022* (2013.01); *B65D 2565/388* (2013.01); *B65D 2577/043* (2013.01)

(58) Field of Classification Search
USPC ......... 206/557, 558, 559, 560, 561, 562, 507, 206/364; 220/529, 629
See application file for complete search history.

(56) References Cited

U.S. PATENT DOCUMENTS

| 2,655,283 | A |   | 10/1953 | Moldt |         |
|-----------|---|---|---------|-------|---------|
| RE27,649  | E | * | 5/1973  | Levenhagen | 206/507 |
| 4,316,540 | A | * | 2/1982  | Lapham | 206/507 |

(Continued)

FOREIGN PATENT DOCUMENTS

WO  WO-2009/015862 A1  2/2009

OTHER PUBLICATIONS

PCT International Search Report and Written Opinion dated Apr. 7, 2011 issued in PCT International Patent Application No. PCT/EP2011/056861 filed Apr. 29, 2011.

*Primary Examiner* — Jacob K Ackun
(74) *Attorney, Agent, or Firm* — Locke Lord LLP

(57) ABSTRACT

Packaging structure for containers (3, 3') for pharmaceutical use, comprising a tray (1) having an open side for introducing and extracting a support plane (2) of the containers (3, 3'), and a closing element (5) of the open side of the tray (1), said support plane (2) having a spatial prefixed distribution of seats (6) in which said containers (3, 3') can be precisely positioned without mutual contact, whereby the structure comprises diversification means of the engaging configuration between said support plane (2) and said tray (1) in order to maintain unchanged the points inside the tray (1) in which an end (3a, 3a1) of the containers (3, 3') is placed, with the variation of the height of the containers (3, 3') associated from time to time to the support plane (2).

13 Claims, 8 Drawing Sheets

Fig. 1

(51) Int. Cl.
*B65D 77/20* (2006.01)
*B65D 85/42* (2006.01)

(56) References Cited

U.S. PATENT DOCUMENTS

| | | | |
|---|---|---|---|
| 5,004,103 A * | 4/1991 | Connors et al. | 206/372 |
| 5,910,162 A * | 6/1999 | Harbour et al. | 62/246 |
| 5,912,033 A * | 6/1999 | Ferguson | 426/124 |
| 5,950,832 A * | 9/1999 | Perlman | 206/446 |
| 6,146,673 A * | 11/2000 | Ferguson | 426/115 |
| 6,153,237 A * | 11/2000 | Ferguson | 426/115 |
| 6,164,044 A * | 12/2000 | Porfano et al. | 53/471 |
| 6,585,942 B1* | 7/2003 | Bussell et al. | 422/300 |
| 8,474,617 B2* | 7/2013 | Wiedmann et al. | 206/427 |
| 8,490,790 B2* | 7/2013 | Cocheteux et al. | 206/366 |
| 8,573,437 B1* | 11/2013 | Evans | 220/737 |
| 2005/0193586 A1* | 9/2005 | Yarborough et al. | 34/285 |
| 2007/0144935 A1* | 6/2007 | Davis et al. | 206/562 |
| 2008/0217206 A1* | 9/2008 | Shen | 206/562 |

* cited by examiner

PACKAGING STRUCTURE FOR CONTAINERS FOR PHARMACEUTICAL USE

The present invention refers to a packaging structure for containers for pharmaceutical use.

A packaging structure for containers for pharmaceutical use is known, comprising a tray supporting in its inside a support plane having a plurality of housing holes in which the containers are positioned with a vertical orientation.

Some containers like syringes can be held in position by resting their flange on the peripheral edge of the housing holes.

Other containers which do not have protruding parts need suitable elements, permitting them to be held inside the housing holes.

Packaging systems for containers of this kind are known for example from the international patent application n. WO2009/015862.

The known packaging structures have a limited flexibility of use, because they are not suitable generally to be used efficiently and universally for packaging different sets of containers in which the containers of a set differ from those of another set in shape and/or size, generally in height, and in case they are suitable for such a use, they are not able to permit in any case the automatic management of the various sets of containers, by means of processing machines intended for their handling, filling and eventual closure.

The technical scope of the present invention is a packaging structure for containers for a pharmaceutical use, which permits the elimination of the technical drawbacks of the prior art.

In view of the above, it is one object of the invention to provide a packaging structure for containers for pharmaceutical use, which can be universally used to package sets of containers in which each set differs from the other with respect to the height of the containers, and at the same time permits the automatic management of the specific set of containers.

Another object of the invention is to provide a packaging structure for containers for pharmaceutical use able to hold the containers firmly in a prefixed position in order to protect them from accidental breakage and in order to enable their management in an automatic way with a processing machine.

Another object of the invention is to provide a packaging structure for containers for pharmaceutical use, which guarantees the sterilization of the product, the maintenance of its sterility, its quality properties, the evidence of the integrity of the product, the identification and the traceability of the product, and the transfer of the product, without compromising the previously listed properties. These objects and other objects according to the present invention are achieved by a packaging structure for containers for pharmaceutical use, comprising a tray having an open side for introducing and extracting a support plane for containers, and a closing element at the open side of the tray, said support plane having a spatially prefixed distribution of seats in which said containers can be precisely positioned without mutual contact, at a mutual distance, characterized in that the tray comprises differentiating means for engaging configurations between said support plane and said tray in order to maintain the points inside the tray in which the tops of the containers are placed unchanged, while varying the height of the sets of containers placed in the support plane.

Preferably the support plane of the containers can be positioned parallel to the resting plane of the tray, and the containers can be positioned in said seats with their longitudinal axis orthogonal to the resting plane of the tray, and the differentiating means modify the engaging position of said support plane in said tray, along the direction orthogonal to the resting plane of said tray.

The differentiating means preferably include protrusions, which can engage in corresponding recesses.

Preferably said recesses are positioned along the edge of said support plane and said protrusions are positioned along the inner surface of the lateral walls of said tray, or vice versa.

Preferably said support plane has a first engaging position at a first distance from the base of said tray when said protrusions are engaged in said recesses and the edge of the support plane rests on an inner peripheral shoulder of the lateral walls of said tray, and a second engaging position at a second distance from the base of said greater tray of said first distance, when said recesses are disengaged from said protrusions on which the edge of said support plane rests.

Preferably said protrusions and said recesses are positioned such that said first and second engaging positions are obtained by a 180° rotation of said support plane with respect to said tray, around its central axis, orthogonal to the resting plane of the tray.

Preferably said seats comprise circular through holes, disposed in a matrix.

Preferably said support plane has, at each circular through hole, a system for sustaining a container.

Preferably said system has a resting portion, within the cylindrical space defined by the cylindrical generating elements of said circular hole, and said resting system is configured to leave a diametric plane of said cylindrical space unobstructed.

Preferably the unobstructed diametric spaces, corresponding to the holes of each row of holes are mutually coplanar.

Preferably an unobstructed total volume is associated with the unobstructed diametric coplanar planes, so to permit the introduction from below of a rising element, for simultaneous action on one or more containers.

Preferably said closing element is a sheet of foil.

Preferably said closing element is made from a selective material permeable to a gas use for the sterilization of the contents of the tray.

Preferably the tray has a protective envelope to be transferred in a controlled zone.

Preferably an identification and traceability element is associated with the tray. Further characteristics and advantages of the invention will be clearer from the description of a preferred but not limiting embodiment of the packaging structure for containers for pharmaceutical use, shown in an indicative and non limiting way in the annexed drawings, in which:

FIG. 4b shows a top side view of the tray with the support plane in the second engaging position in which it houses a set of containers of a height lower than those shown in FIG. 4a;

Figure 1:
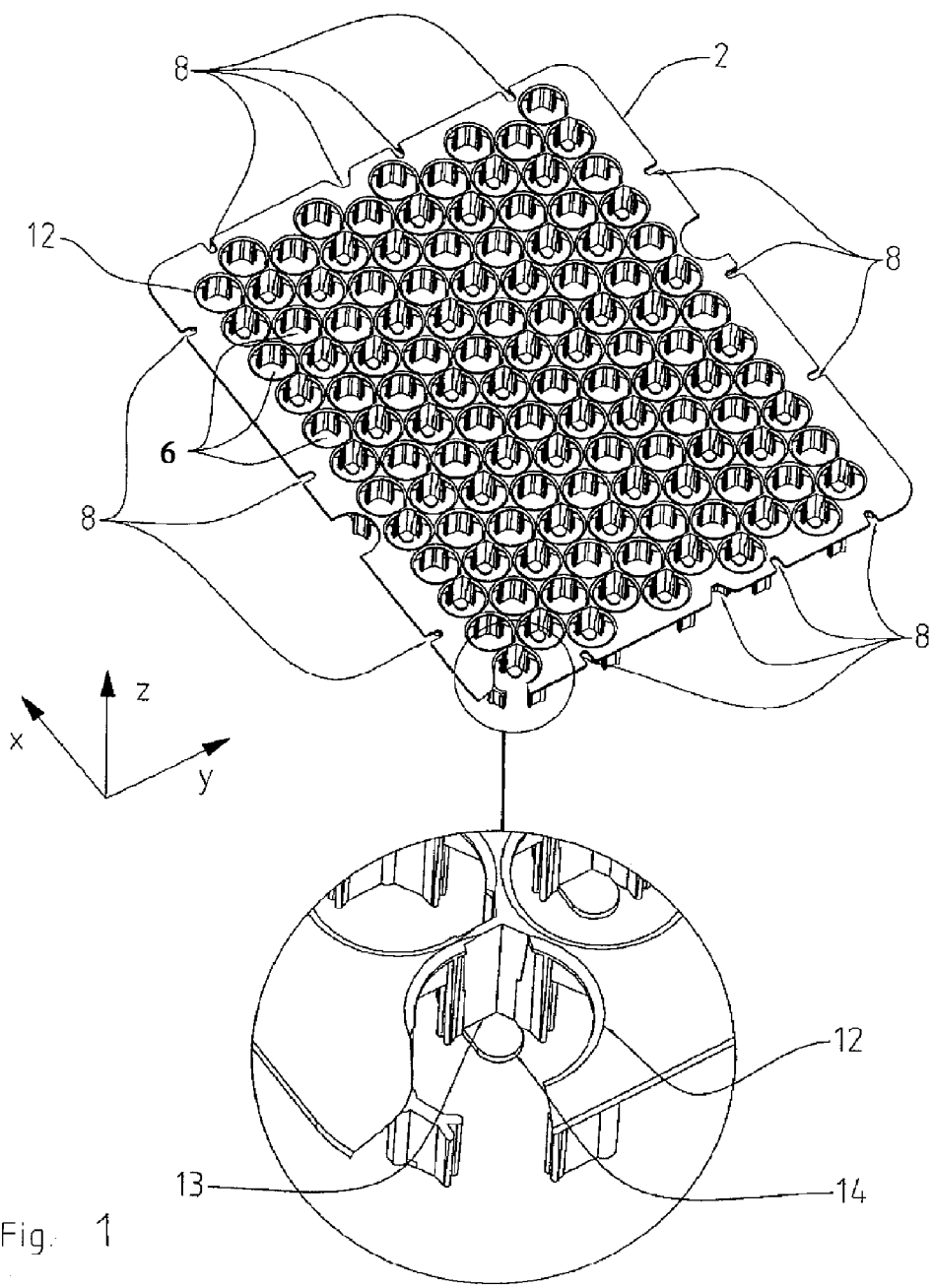
FIG. 1 shows a perspective view of the support plane without containers, and one enlarged detail of the same.
Figure 2:
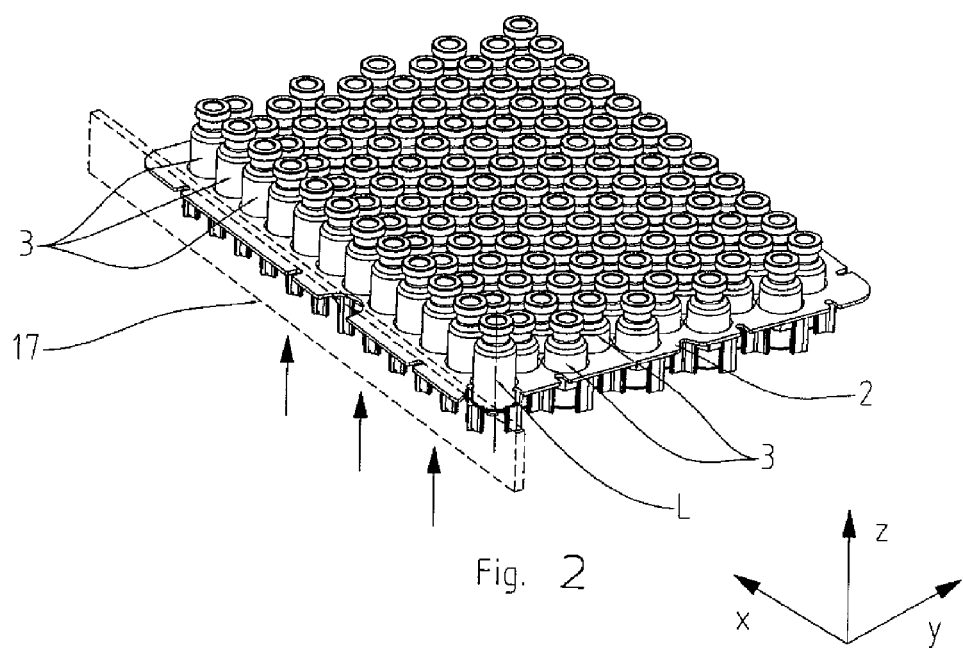
FIG. 2 shows a perspective view of a portion of the support plane with the containers housed therein and a handling beam of the rows of containers.
Figure 3:
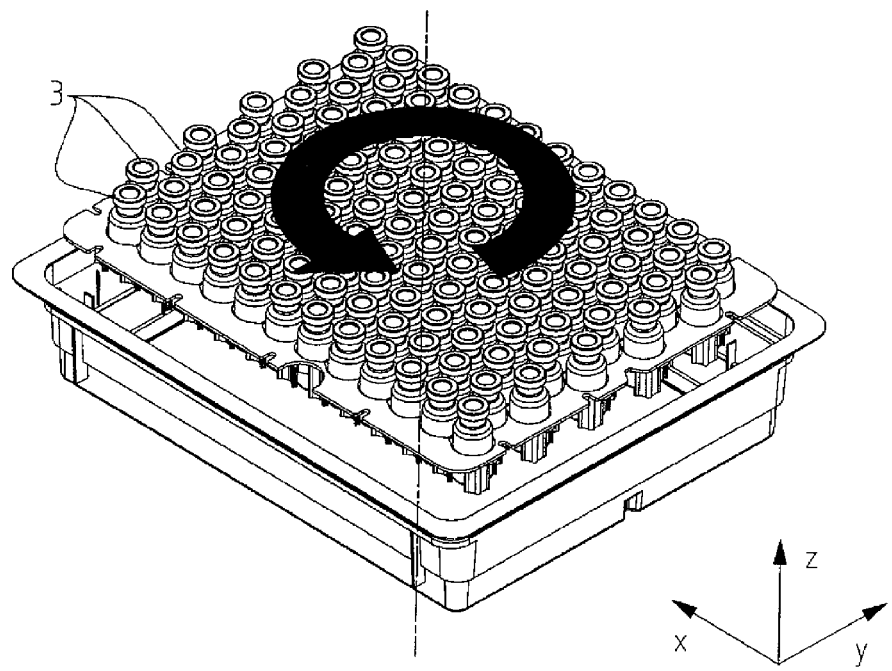
FIG. 3 shows a perspective view of the tray with a set of identical containers of a certain height.
Figure 3:
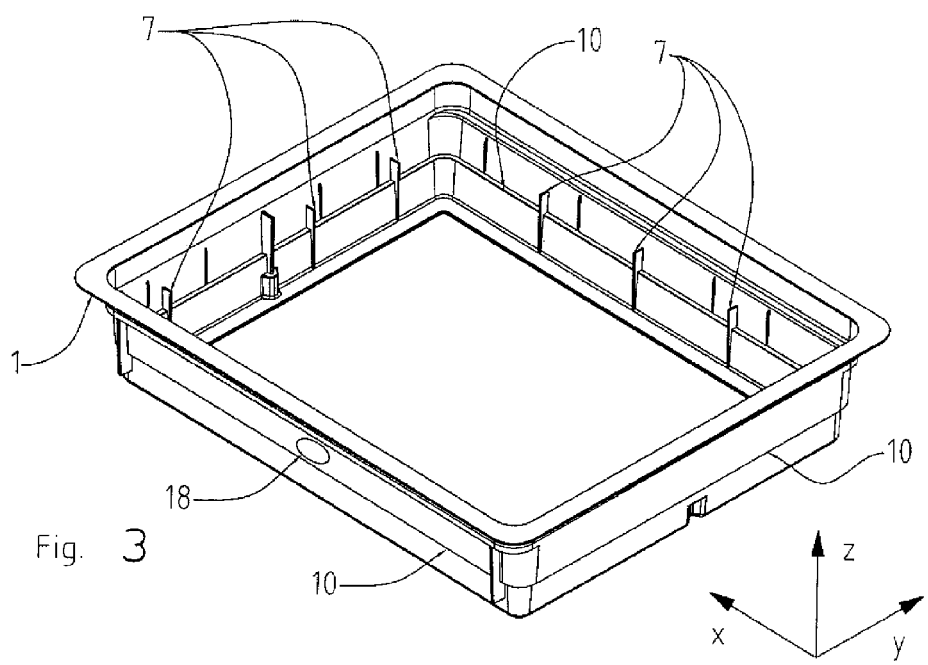

With reference to the cited figures, a packaging structure for containers for pharmaceutical use, for example, glass or plastic bottles, is shown.

The packaging structure comprises a tray 1 having an open side for inserting and removing a support plane 2 for the containers 3, 3' which can be positioned parallel with the resting plane 4 of the tray 1, and with a closing element 5 on the open side of the tray 1.

The support plane 2 has a spatially prefixed distribution of seats 6 in which the containers 3, 3' can be positioned at a mutual distance with their longitudinal axis L, L' orthogonal to the resting plane 4 of the tray 1.

The support plane 2 has a quadrangular shape with pairs of opposed parallel edges 2a, 2a, and 2b, 2b.

Analogously the tray 1 has a quadrangular shape with a base 9 provided parallel to the resting plane 4 and pairs of opposed lateral walls 1a, 1a and 1b, 1b.

The packaging structure comprises differentiating means of the engaging configuration between the support plane 2 and the tray 1 able to modify the engaging position of the support plane 2 in the tray 1 along the Z-axis orthogonal to the resting plane 4 of the tray 1 in order to maintain the points of which the tops 3a, 3a' of the containers 3, 3' are positioned inside the tray unchanged while varying of the height of the containers 3, 3' of the container set 3, 3'.

The differentiating means are now explained in more detail in order to guarantee the drive and the alignment of the containers 3, 3' during the various phases of the process.

It is clear that the height of the containers 3, 3' corresponds to their size in the direction of their longitudinal axis L, L'.

Figure 4A:
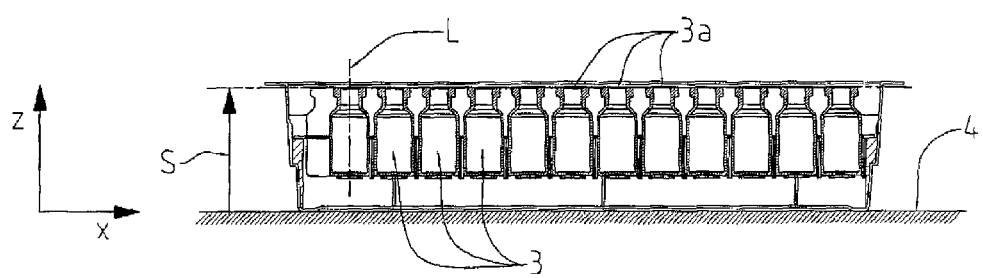
FIG. 4a shows a top side view of the tray with the support plane in the first engaging position in which it houses a set of containers of a certain height.
Figure 4B:
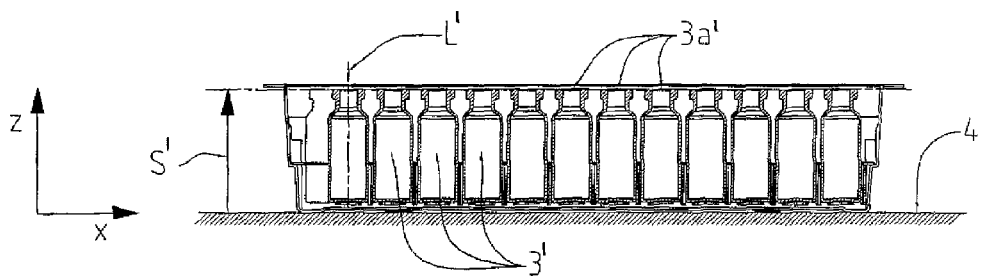
Figure 6:
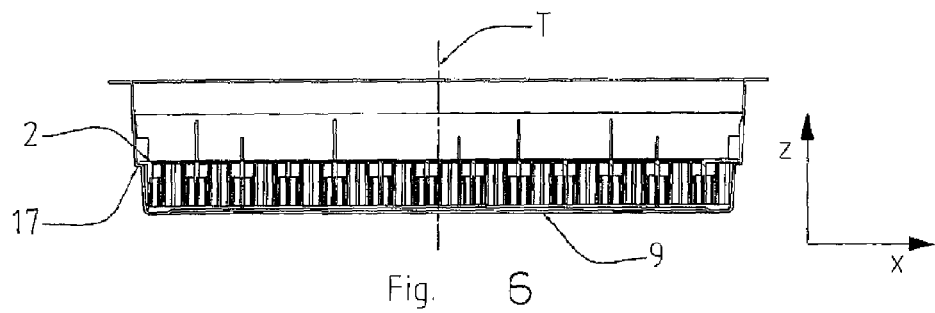
FIG. 6 shows a top side view of the tray, sectioned along the line 6-6 in FIG. 5.

From the comparison between FIGS. 4a and 4b it can be seen that the distance S to the top 3a of a container 3 from the base 9 of the tray 1 corresponds to the distance S' to the top 3a' of a container 3' from the base 9 of the tray 1.

The differentiating means comprise protrusions 7 provided on the tray 1 which can engage in recesses 8 provided on the support plane 2.

The support plane 2 has a first engaging position at a first distance from the base 9 of the tray 1 when the protrusions 7 are engaged in the recesses 8 and the edge of the support plane 2 rests on an inner peripheral shoulder 10 of the lateral walls 1a, 1a and 1b, 1b of the tray 1, and a second engaging position at a second distance from the bottom 9 of the tray 1 greater than the first distance, in which the recesses 8 are disengaged from the protrusions 7 and in which the edge of the support plane 2 is resting on the protrusions 7.

The recesses 8 are positioned along the pairs of opposed parallel edges 2a, 2a and 2b, 2b of the support plane 2 whereas the protrusions 7 are positioned along the inner surface of the lateral walls 1a, 1a and 1b, 1b of the tray 1.

In particular, a first lateral wall 1a of the tray 1 has three protrusions 7 and a second lateral wall 1a has three protrusions 7 offset from those of the first lateral wall 1a along the common direction of the first and second lateral walls 1a.

A first lateral wall 1b of the tray 1 has four protrusions 7 and a second lateral wall 1b has four protrusions 7 offset from those of the first lateral wall 1b along the common direction of the first and second lateral wall 1b.

A first edge 2a of the support plane 2 has four recesses 8 and a second edge 2a of the support plane 2 has three recesses 8 offset from those of the first edge 2a along the common direction of the edges 2a.

A first edge 2b of the support plane 2 has four recesses 8 and a second edge 2b of the support plane 2 has four recesses 8 offset from those of the first edge 2b along the common direction of the edges 2b.

The protrusions 7 and the recesses 8 are positioned so that the change between the first and second engaging position is effected by rotating of the support plane 2 with respect to the tray 1 by 180° around its central axis T orthogonal to the resting plane 4 of the tray 1.

In practice, when the protrusions 7 are aligned with the recesses 8, the latter can slide along the protrusions 7 which extend themselves again longitudinally along the direction Z orthogonal to the resting plane 4, and the support plane 2 can move towards the base 9 of the tray 1 until it rests on the shoulder 10.

On the other hand, when the protrusions 7 are not aligned with the recesses 8, the support plane 2 rests on the protrusions 7.

The system can be better understood through the use of a Cartesian reference system in which the X and Y axes form a plane, corresponding to the resting plane 4 in which the base 9 of the tray 1 is housed and Z, as aforesaid, is orthogonal to the resting plane 4.

In order to guarantee that the points inside the tray 1 remain unchanged when the height of the containers 3, 3' of the set of containers (size along the axis Z of the containers 3, 3' when associated to their seats 6), is varied the distribution of the seats 6 in the plane XY must be such as to reproduce itself when rotated around the Z-axis.

The seats 6 comprise circular through holes 12 with a matrix arrangement in directions X and Y.

Each hole 12 comprises a system for resting a container 3, 3', in particular a foot 13.

The foot 13 has a resting portion 14 contained in the cylindrical space 15 defined by the generation lines of the hole 12 parallel with the axis Z.

Advantageously the portion 14 of the foot 13 is configured in order to free a diametric plane 16 of the cylindrical space 15, e.g. leave diametric plane 16 unobstructed.

Figure 5:
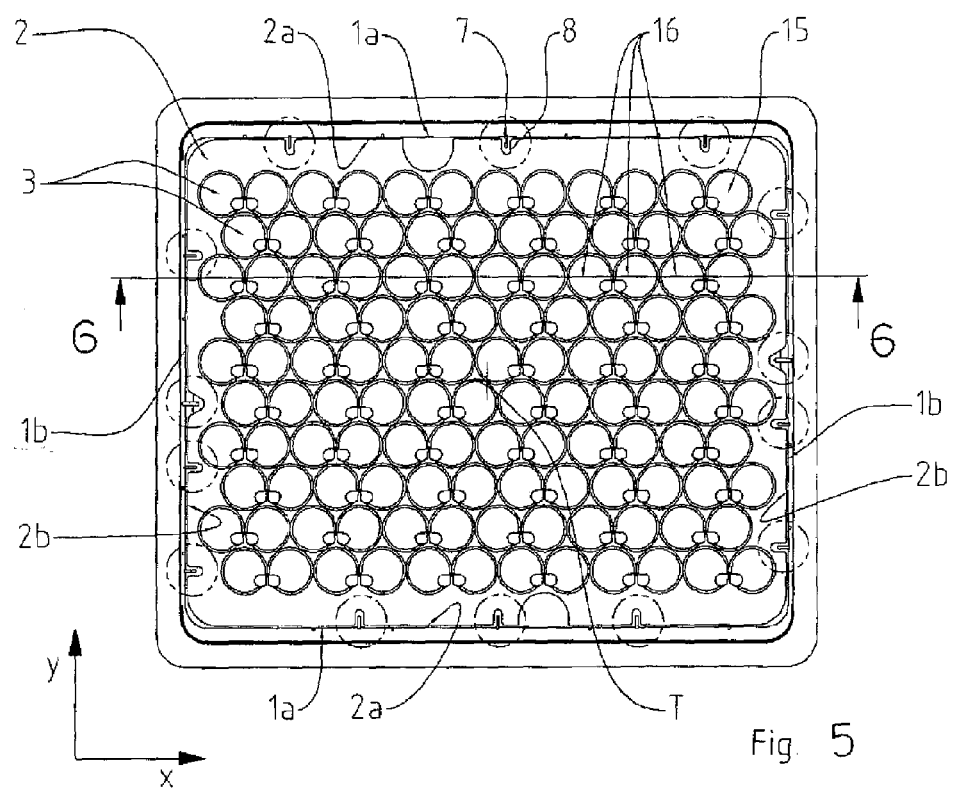
FIG. 5 shows a plan view of the tray without containers with the support plane in its first engaging position.
Figure 8:
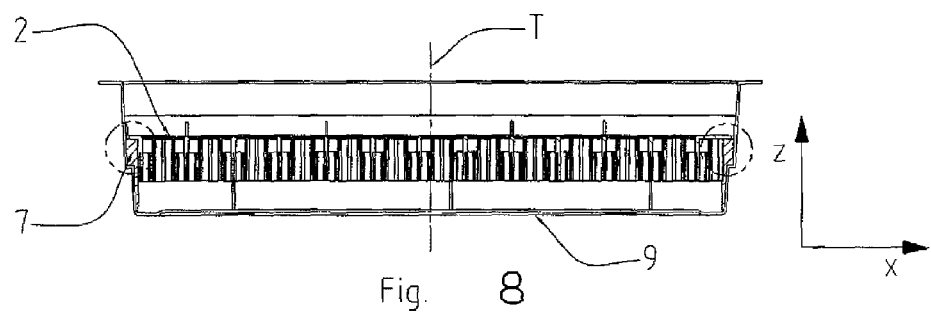
FIG. 8 shows a top side view of the tray, sectioned along the line 8-8 in FIG. 7.
Figure 7:
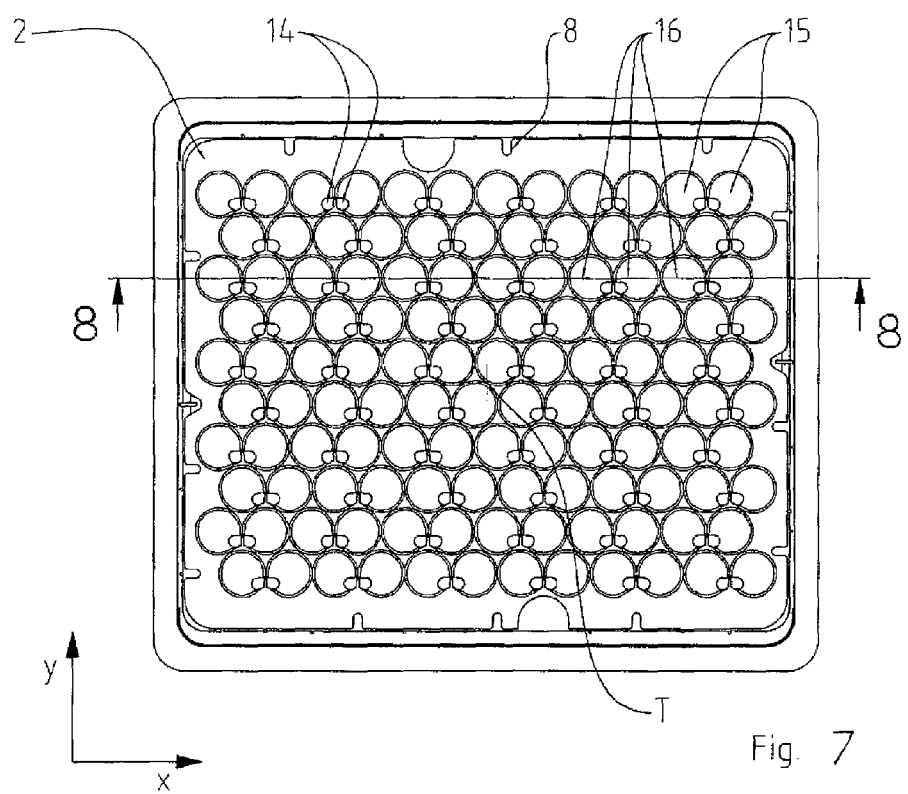
FIG. 7 shows a plan view of the tray with the support plane in its second engaging position.
Figure 9:
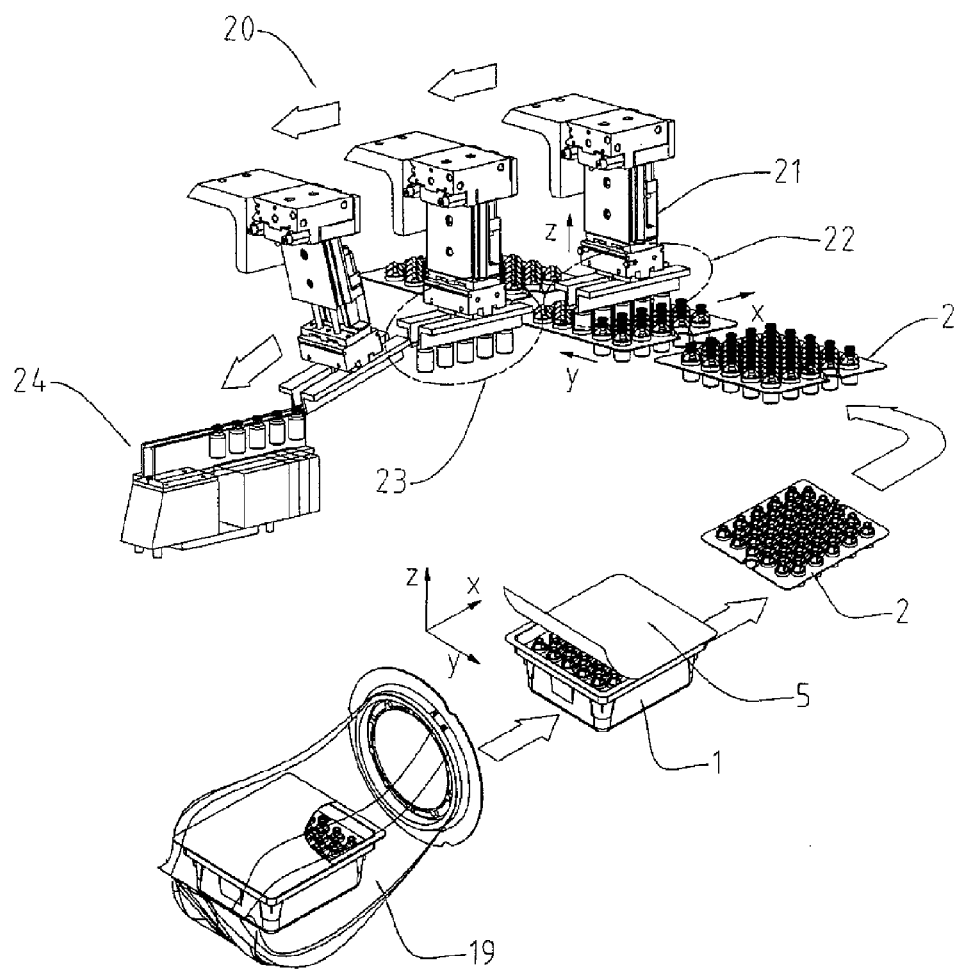
FIG. 9 shows a possible automatic handling layout of the containers, with a processing machine.

More precisely, the unobstructed diametric planes 16 corresponding to holes 12 of each row of holes 12 are mutually coplanar. In the FIGS. 5 and 7 they occupy parallel planes with respect to the axis XZ. This permits the automatic handling of the containers 3, 3' in rows, by means of a beam 17 positioned under the support plane 2, when this is extracted from the tray 1. The beam 17 is placed longitudinally along the axis X under a row of containers 3, 3' in the direction of the X-axis, and it can be moved in the direction of the Z-axis. The closing element 5 is a foil sheet realized in a selectively permeable material permeable to a sterilization process for the containers in the tray 1. An identification and traceability element 18 is associated with the tray 1, and the identification and traceability element 18 can, for example, be a code which can be decoded by means of RFID technology.

The tray 1 can have a housing 19 for protecting its transfer in a controller zone (for example in an area where the filling of the containers occurs).

The protective housing 19 can be closed or open and in particular it can be provided or not with a rapid transfer gate. Each protective housing 19 can contain one or more stacked trays 1, and it is formed, at least for one portion, by a sheet realized of a selectively permeable material permeable to a sterilization process for the contents of the tray 1.

The packaging structure is used for feeding directly and in an automatic way the containers 3, 3' with a spatially prefixed orientation to a processing machine 20 for their handling.

The processing machine 20 can operate in the same way both in presence of containers 3, and of containers 3' because they are directed to the processing machine 20 with their tops 3a, 3a' in the same positions even if they have a different height (see a comparison between FIGS. 4a and 4b).

The processing machine 20 comprises a robot arm 21 having a head 22 for handling the containers 3, 3'.

The robot arm 21 has a horizontal translation axis in the direction of the X-axis, a vertical translation axis in the direction of the Z-axis and a rotary axis corresponding to the rotary axis Y.

The handling head 22 has a rectilinear open groove 23 for handling a row of containers 3, 3'.

The support plane 2, after having been extracted from the outer housing 19 and freed from the closing element 5, is handled towards the handling position by means of the handling head 22 in which the containers 3, 3' are directed, in rows oriented along the axis X.

In particular the handling head 22 is initially above the support plane 2 and it has the groove 23 oriented parallel to the X axis.

The handling head 22 performs a translation along the X axis in order to insert the necks of the row of containers 3, 3' aligned with the grove 23 into the groove 23.

In order to facilitate the extraction of the containers 3, 3' the beam 17 which is oriented parallel to the X-axis is actuated in the direction of the Z-axis. The beam 17 causes a partial extraction of the row of containers 3, 3' which the handling head 22 then catches.

After having picked up the row of containers 3, 3' the handling head 22 performs a translation in the direction of the Z axis in order to lift the row of containers 3, 3' which are completely separated from the support plane 2.

Later on, the handling head 22 performs a translation along the X axis, in order to transport the row of containers 3, 3' towards a conveying station 24 at which the handling head 22 rotates around the Y axis in order to discharge the row of containers 3, 3' in the conveyor station 24.

Figure 10:
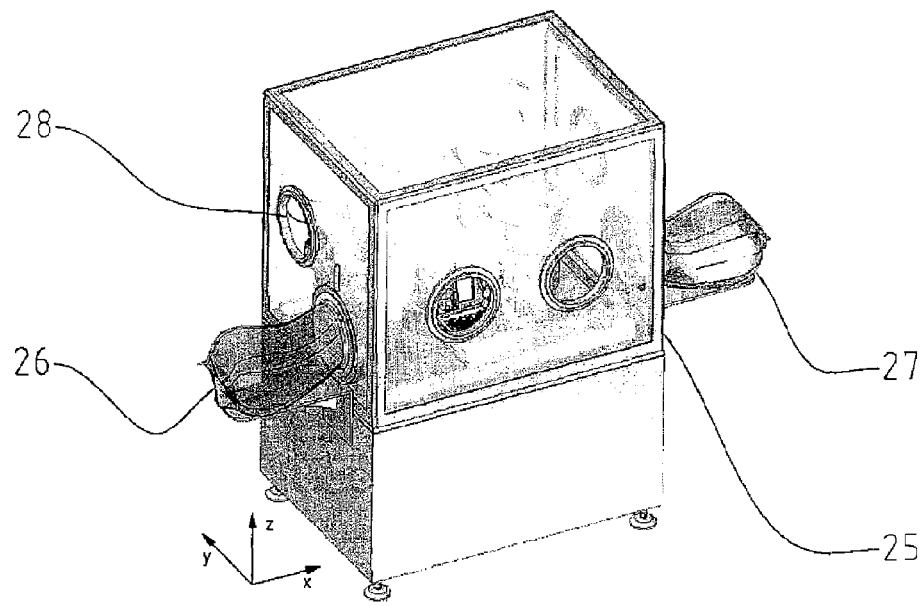
FIGS. 10 and 11 show a different processing machine, shown with and without an insulator for clarity's sake, suitable to process the containers according to the present invention.
Figure 11:
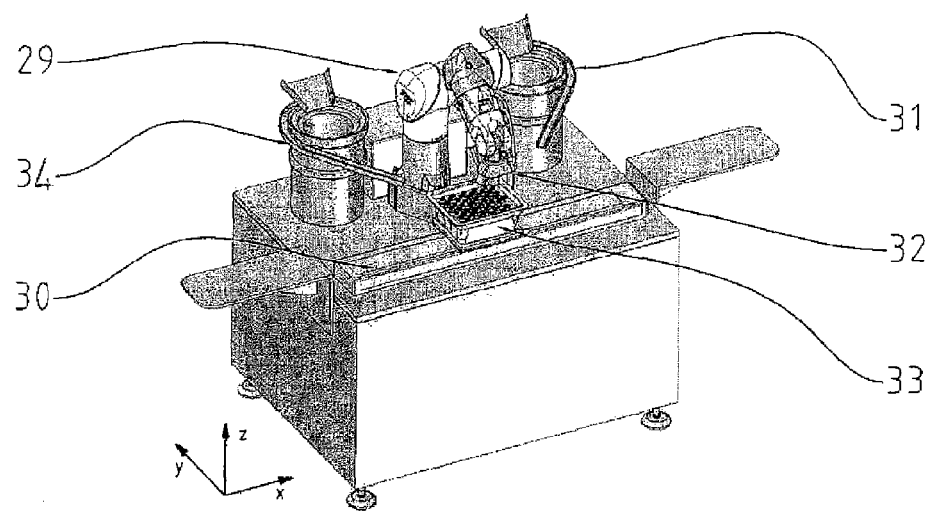

With reference to FIGS. 10 and 11, the processing machine comprises an insulating cover 25 with a vertical, laminar airflow downwards, in order to keep the inside of the containers 3, 3' clean.

The cover 25 has an inlet rapid transferring gate 26 for the containers 3, 3' and an outlet rapid transferring gate 27 for the containers 3, 3', besides other gates, for example, a gate 28 for a handling by means of a glove (not shown).

The processing machine has a translation slide 30 with a movement directed step by step, in order to bring the containers 3, 3' from the inlet gate 26 to the reference position, under an anthropomorphic robot 29 and from there to the outlet gate 27.

At the opposite sides of the robot 29 a first vibration distributor 34, and a second vibration distributor 31 are provided. They contain accessories to be applied to the containers 3, 3', for example plugs and ring crimps.

The robot is able to recognize the position of the containers 3, 3', because they have a prefixed spatial position, and by means of a manipulator 32 fills them, closes them with a plug taken from one of the distributors, and finally hermetically seals the plug by applying a crimp ring.

The packaging structure for containers for pharmaceutical use so conceived is susceptible of various changes and variants, all in the scope of the inventive object; furthermore all the details can be substituted by technical equivalent elements. For example, the number of engaging positions of the support plane with the tray can be greater than two, the passage among the various engaging configurations can be obtained also with a rotary translation movement of the support plane also different from the shown one, and also the structure of the differentiating means. In practice, the materials used, and also the sizes can be of any kind, according to the needs and to the state of the art.

The invention claimed is:

1. A packaging structure for containers for pharmaceutical use, pretreated, sterile and ready to be used, comprising:
a support plane having a spatial prefixed distribution of seats to accommodate precise positioning of containers without mutual contact, wherein said seats include circular through holes disposed in a matrix, and said support plane has, at each hole, a respective system configured to sustain the containers, wherein each system includes a resting portion within the respective cylindrical space defined by each hole and wherein a respective diametric plane through each cylindrical space is unobstructed; and
a tray having an open side for introducing and extracting said support plane, and a closing element at the open side of the tray, wherein the tray includes a differentiating means for engaging configurations between said support plane and said tray in order to maintain the points inside the tray in which tops of the containers are placed unchanged while varying the height of the containers placed in the support plane.

2. The packaging structure for containers for pharmaceutical use according to claim 1, wherein said support plane of the containers is positioned parallel to the resting plane of the tray, wherein said seats are configured to have containers are positioned in said seats with their longitudinal axis orthogonal to the resting plane of the tray, and wherein said differentiating means modify the engaging position of said support plane in said tray along the direction orthogonal to said resting plane of said tray.

3. The packaging structure for containers for pharmaceutical use according to claim 1, wherein said differentiating means includes protrusions which can engage in corresponding recesses.

4. The packaging structure for containers for pharmaceutical use according to claim 3, wherein said recesses are positioned along the edge of said support plane and said protrusions are positioned along the inner surface of the lateral walls of said tray or vice versa.

5. The packaging structure for containers for pharmaceutical use according to claim 3, wherein said support plane has a first engaging position at a first distance from the base of said tray when said protrusions are engaged in said recesses and the edge of said support plane rests on an inner peripheral shoulder of the lateral walls of said tray, and a second engaging position at a second distance of said tray that is greater than the first distance when said recesses are disengaged from said protrusions on which the edge of said support plane rests.

6. The packaging structure for containers for pharmaceutical use according to claim 5, wherein said protrusions and said recesses are positioned so that said first and second engaging positions are obtained by a 180° rotation of said support plane with respect to said tray around its central axis orthogonal to the resting plane of the tray.

7. The packaging structure for containers for pharmaceutical according to claim 1, wherein the unobstructed diametric planes corresponding to holes of each row of holes are mutually coplanar.

8. The packaging structure for containers for pharmaceutical use according to claim 7, wherein an unobstructed total volume is associated with the unobstructed and coplanar diametric planes, in order to permit the introduction from below of a rising element for a simultaneous action on one or more containers.

9. The packaging structure for containers for pharmaceutical use according to claim 1, wherein said closing element is a foil sheet.

10. The packaging structure for containers for pharmaceutical use according to claim 1, wherein said closing element is of a selective material permeable to a sterilization process of the contents of the tray.

11. The packaging structure for containers for pharmaceutical use according to claim 1, further comprising at least one of a closed protective housing, wherein the closed protective housing guarantees the sterility of the tray, or a housing having at least one rapid transferring gate for introduction of containers in a controlled zone.

12. The packaging structure for containers for pharmaceutical use, according to claim 1, wherein the tray is operatively connected to an identification and traceability element.

13. A packaging structure for containers for pharmaceutical use, pretreated, sterile and ready to be used, comprising:
   a support plane having a spatial prefixed distribution of seats to accommodate precise positioning of containers without mutual contact, wherein said seats include circular through holes disposed in a matrix, and said support plane has, at each hole, a respective system configured to sustain the containers, wherein each system includes a resting portion extending radially inward within the respective cylindrical space defined by each hole and wherein a respective diametric plane through each cylindrical space is unobstructed; and
   a tray having an open side for introducing and extracting said support plane, and a closing element at the open side of the tray, wherein the tray includes a differentiating means for engaging configurations between said support plane and said tray in order to maintain the points inside the tray in which tops of the containers are placed unchanged while varying the height of the containers placed in the support plane.

* * * * *